(12) United States Patent
Sicvol (10) Patent No.: US 9,924,966 B2
(45) Date of Patent: Mar. 27, 2018

(54) ARTICULATING CANNULA ACCESS DEVICE

(71) Applicant: Atricure, Inc., Mason, OH (US)

(72) Inventor: Christopher W. Sicvol, Durham, NC (US)

(73) Assignee: AtriCure, Inc., Mason, OH (US)

( * ) Notice: Subject to any disclaimer, the term of this patent is extended or adjusted under 35 U.S.C. 154(b) by 175 days.

(21) Appl. No.: 14/509,789

(22) Filed: Oct. 8, 2014

(65) Prior Publication Data

US 2015/0119642 A1  Apr. 30, 2015

Related U.S. Application Data

(63) Continuation of application No. 12/108,426, filed on Apr. 23, 2008, now Pat. No. 8,858,528.

(51) Int. Cl.
| | |
|---|---|
| *A61B 1/005* | (2006.01) |
| *A61B 17/34* | (2006.01) |
| *A61B 1/00* | (2006.01) |
| *A61B 1/32* | (2006.01) |
| *A61B 1/05* | (2006.01) |
| *A61B 17/02* | (2006.01) |
| *A61B 17/00* | (2006.01) |

(52) U.S. Cl.
CPC ...... *A61B 17/3423* (2013.01); *A61B 1/00105* (2013.01); *A61B 1/05* (2013.01); *A61B 1/32* (2013.01); *A61B 17/0218* (2013.01); *A61B 17/3421* (2013.01); *A61B 2017/00331* (2013.01); *A61B 2017/00991* (2013.01); *A61B 2017/0225* (2013.01); *A61B 2017/3425* (2013.01); *A61B 2017/3443* (2013.01)

(58) Field of Classification Search
CPC ........... A61B 2017/00331; A61B 2017/00991; A61M 25/0147; A61M 25/0152; A61M 2025/0161

See application file for complete search history.

(56) References Cited

U.S. PATENT DOCUMENTS

| | | |
|---|---|---|
| 3,470,876 A | 10/1969 | Barchilon |
| 4,040,413 A | 8/1977 | Ohshiro |
| 4,576,162 A | 3/1986 | McCorkle |
| 4,688,554 A | 8/1987 | Habib |
| 4,690,411 A | 9/1987 | Van Winkle |
| 4,719,924 A | 1/1988 | Crittenden et al. |
| 4,777,951 A | 10/1988 | Cribier et al. |
| 4,898,577 A | 2/1990 | Badger et al. |

(Continued)

FOREIGN PATENT DOCUMENTS

| | | |
|---|---|---|
| EP | 0135364 | 3/1985 |
| EP | 1935348 | 6/2008 |

(Continued)

OTHER PUBLICATIONS

Cragg, et al., "Endovascular diathermic vessel occlusion," *Radiology*, 144:303-308, 1982.

(Continued)

*Primary Examiner* — Aarti B Berdichevsky
(74) *Attorney, Agent, or Firm* — Levine Bagade Han LLP (57) ABSTRACT

Devices and methods are disclosed for less invasive surgery. More particularly, methods and devices described herein permit improved access within a body cavity when performing a minimally invasive procedure, typically through a small opening, a surgical port, or during an open surgical procedure.

13 Claims, 8 Drawing Sheets

(56) References Cited

U.S. PATENT DOCUMENTS

| | | |
|---|---|---|
| 4,920,980 A | 5/1990 | Jackowski |
| 4,921,482 A | 5/1990 | Hammerslag et al. |
| 4,960,134 A | 10/1990 | Webster |
| 4,960,411 A | 10/1990 | Buchbinder |
| 4,976,688 A | 12/1990 | Rosenblum |
| 4,998,916 A | 3/1991 | Hammerslag et al. |
| 5,025,778 A | 6/1991 | Silverstein et al. |
| 5,030,204 A | 7/1991 | Badger et al. |
| 5,037,391 A | 8/1991 | Hammerslag et al. |
| 5,125,395 A | 6/1992 | Adair |
| 5,199,950 A | 4/1993 | Schmitt et al. |
| 5,203,767 A | 4/1993 | Cloyd |
| 5,205,816 A | 4/1993 | Dodson et al. |
| 5,209,736 A | 5/1993 | Stepens et al. |
| 5,235,966 A | 8/1993 | Jamner |
| 5,275,608 A | 1/1994 | Forman et al. |
| 5,282,826 A | 2/1994 | Quadri |
| 5,308,316 A | 5/1994 | Williams et al. |
| 5,322,064 A | 6/1994 | Lundquist |
| 5,325,845 A | 7/1994 | Adair |
| 5,330,502 A | 7/1994 | Hassler et al. |
| 5,374,277 A | 12/1994 | Hassler |
| 5,378,234 A | 1/1995 | Hammerslag et al. |
| 5,399,161 A | 3/1995 | Williams et al. |
| 5,453,078 A | 9/1995 | Valentine et al. |
| 5,460,621 A | 10/1995 | Gertzman et al. |
| 5,571,088 A | 11/1996 | Lennox et al. |
| 5,618,294 A | 4/1997 | Aust et al. |
| 5,634,937 A | 6/1997 | Mollenauer et al. |
| 5,637,097 A | 6/1997 | Yoon |
| 5,651,366 A | 7/1997 | Liang et al. |
| 5,658,307 A | 8/1997 | Exconde |
| 5,704,534 A | 1/1998 | Huitema et al. |
| 5,725,523 A | 3/1998 | Mueller |
| 5,783,227 A | 7/1998 | Dunham |
| 5,785,706 A | 7/1998 | Bednarek |
| 5,829,447 A | 11/1998 | Stevens et al. |
| 5,843,017 A | 12/1998 | Yoon |
| 5,865,802 A | 2/1999 | Yoon et al. |
| 5,899,914 A | 5/1999 | Zirps et al. |
| 5,919,188 A | 7/1999 | Shearon et al. |
| 5,967,997 A | 10/1999 | Turturro et al. |
| 5,980,455 A | 11/1999 | Daniel et al. |
| 6,077,287 A | 6/2000 | Taylor et al. |
| 6,080,151 A | 6/2000 | Swartz et al. |
| 6,126,649 A | 10/2000 | VanTassel et al. |
| 6,161,543 A | 12/2000 | Cox et al. |
| 6,176,825 B1 | 1/2001 | Chin et al. |
| 6,203,559 B1 | 3/2001 | Davis et al. |
| 6,234,958 B1 | 5/2001 | Snoke et al. |
| 6,264,654 B1 | 7/2001 | Swartz et al. |
| 6,314,963 B1 | 11/2001 | Vaska et al. |
| 6,330,965 B1 | 12/2001 | Milliman et al. |
| 6,332,881 B1 | 12/2001 | Carner et al. |
| 6,364,876 B1 | 4/2002 | Erb et al. |
| 6,463,332 B1 | 10/2002 | Aldrich |
| 6,478,028 B1 | 11/2002 | Paolitto et al. |
| 6,484,727 B1 | 11/2002 | Vaska et al. |
| 6,506,200 B1 | 1/2003 | Chin |
| 6,514,250 B1 | 2/2003 | Jahns et al. |
| 6,530,914 B1 | 3/2003 | Mickley |
| 6,551,337 B1 | 4/2003 | Rabiner et al. |
| 6,558,382 B2 | 5/2003 | Jahns et al. |
| 6,592,547 B2 | 7/2003 | Grimes et al. |
| 6,592,604 B2 | 7/2003 | Hess et al. |
| 6,663,641 B1 | 12/2003 | Kovac et al. |
| 6,666,854 B1 | 12/2003 | Lange |
| 6,726,684 B1 | 4/2004 | Woloszko et al. |
| 6,752,756 B2 | 6/2004 | Lunsford et al. |
| 6,887,249 B1 | 5/2005 | Houser et al. |
| 6,893,442 B2 | 5/2005 | Whayne |
| 6,917,834 B2 | 7/2005 | Koblish et al. |
| 6,953,454 B2 | 10/2005 | Peterson et al. |
| 6,989,018 B2 | 1/2006 | Fogarty et al. |
| 6,991,627 B2 | 1/2006 | Madhani et al. |
| 7,001,404 B1 | 2/2006 | Chin |
| 7,063,698 B2 | 6/2006 | Whayne et al. |
| 7,144,363 B2 | 12/2006 | Pai et al. |
| 7,300,448 B2 | 11/2007 | Criscuolo et al. |
| 7,300,488 B2 | 11/2007 | Szabo et al. |
| 7,328,071 B1 | 2/2008 | Stehr et al. |
| 7,925,341 B2 | 4/2011 | Fuimaono |
| 8,057,465 B2 | 11/2011 | Sliwa et al. |
| 2002/0111637 A1 | 8/2002 | Kaplan et al. |
| 2003/0125664 A1 | 7/2003 | Sydney et al. |
| 2003/0229296 A1 | 12/2003 | Ishikawa et al. |
| 2004/0039339 A1 | 2/2004 | Magnusson |
| 2004/0143257 A1 | 7/2004 | Fuimaono |
| 2004/0216745 A1 | 11/2004 | Chin |
| 2005/0004592 A1 | 1/2005 | Criscuolo |
| 2005/0114342 A1 | 5/2005 | Wesinger et al. |
| 2005/0131403 A1 | 6/2005 | Chang |
| 2005/1020340 | 9/2005 | Butler et al. |
| 2005/0245789 A1 | 11/2005 | Smith et al. |
| 2006/0009762 A1 | 1/2006 | Whayne |
| 2006/0129132 A1 | 6/2006 | Peterson et al. |
| 2006/0183975 A1 | 8/2006 | Saadat et al. |
| 2006/0200124 A1 | 9/2006 | Whayne et al. |
| 2006/0206113 A1 | 9/2006 | Whayne et al. |
| 2006/0235381 A1 | 10/2006 | Whayne et al. |
| 2006/0293646 A1 | 12/2006 | Whayne et al. |
| 2007/0043351 A1 | 2/2007 | Fleischman et al. |
| 2007/0083082 A1 | 4/2007 | Kiser et al. |
| 2007/0083225 A1 | 4/2007 | Kiser et al. |
| 2007/0219550 A1 | 9/2007 | Thompson et al. |
| 2007/0244473 A1 | 10/2007 | Thompson et al. |
| 2007/0249991 A1 | 10/2007 | Whayne et al. |
| 2007/0250058 A1 | 10/2007 | Whayne et al. |
| 2007/0255276 A1 | 11/2007 | Sliwa et al. |
| 2007/0285595 A1 | 11/2007 | Miyamoto et al. |
| 2008/0114288 A1 | 5/2008 | Whayne et al. |
| 2008/0114354 A1 | 5/2008 | Whayne et al. |
| 2008/0114355 A1 | 5/2008 | Whayne et al. |
| 2008/0242940 A1 | 10/2008 | Stefanchik |
| 2008/0243164 A1 | 10/2008 | Stefanchik |
| 2009/0082822 A1 | 3/2009 | Osman |
| 2009/0248055 A1 | 10/2009 | Spivey et al. |
| 2009/0270676 A1 | 10/2009 | Sicvol |
| 2009/0312783 A1 | 12/2009 | Whayne et al. |
| 2010/0049226 A1 | 2/2010 | Shtunilan |
| 2012/0310268 A1 | 12/2012 | Whayne et al. |

FOREIGN PATENT DOCUMENTS

| | | |
|---|---|---|
| WO | WO 1998/34550 | 8/1998 |
| WO | WO 1998/034550 | 8/1998 |
| WO | WO 1999/17665 | 4/1999 |
| WO | WO 1999/017665 | 4/1999 |
| WO | WO 2000/44286 | 8/2000 |
| WO | WO 2000/044286 | 8/2000 |
| WO | WO 2007/037785 | 4/2007 |

OTHER PUBLICATIONS

Gorisch et al., "Heat-induced contraction of blood vessels," *Lasers in Surgery and Medicine*, 2:1-13, 1982.

Nath, et al., "Cellular electrophysiologic effects of hyperthermia on isolated guinea pig papillary muscle: implications for catheter ablation," *Circulation*, 88:1826-1831, 1993.

ARTICULATING CANNULA ACCESS DEVICE

CROSS-REFERENCE TO RELATED APPLICATIONS

The present application is a continuation of U.S. patent application Ser. No. 12/108,426 filed Apr. 23, 2008 now U.S. Pat. No. 8,858,528 issued Oct. 14, 2014), the contents of which are incorporated herein by reference in its entirety.

FIELD OF THE INVENTIONS

Embodiments of the invention relate to methods for minimally invasive surgery and devices useful in such methods. More particularly, methods and devices described herein permit improved access within a body cavity when performing a minimally invasive procedure, typically through a small opening or a surgical port placed in the body to provide access. In such a case, many surgical procedures require treatment of tissue or organs that are not in alignment with an axis of the surgical opening or surgical port. For example, ablation and/or coagulation of tissue during minimally invasive surgical access must often be performed on tissue surfaces that are on a posterior surface of the organ. The ability to advance a rigid device within a body cavity and navigate the device around structures or organs to access a surface that would otherwise be obscured increases the ability of a physician to treat various areas within the body that would otherwise require an open surgical procedure.

DESCRIPTION OF THE RELATED ART

Currently, procedures that provide access to a body cavity involve small incisions rather than creating, significant openings in the body. Clearly, such minimally invasive procedures allow for reduced trauma to the patient, reduced recuperation time, as well as reduced costs of the procedure.

In one example, medical procedures involving the thoracic cavity require openings made through the chest wall. For example, such procedures include median sternotomy, thoracotomy, thoracostomy, or mini-sternotomy. Typically, these surgical techniques require deflation or retraction of the lungs to access the heart and/or other organs within the thoracic space.

A median sternotomy provides the most exposure for the physician. In this procedure the surgeon creates a midline incision through the sternum that cuts along the bone separating it into two sections. With a median sternotomy, although the heart can be lifted and manipulated by hand, the posterior surface of the heart or other organs is still not readily visible unless the heart is significantly rotated or lifted. However, significant rotation or lifting of the heart may cause undesirable hemodynamic issues during beating heart procedures. After the procedure, the surgeon closes the median sternotomy with large diameter metal wires. The rejoined tissue must be held stable during the healing process, similar to a bone fracture that must remain immobile during rehabilitation. Any coughing or dramatic movement is extremely painful to the patient because the chest moves. Clearly, rehabilitation after the medial sternotomy requires a significant amount of time.

Thoracotomy techniques involve creating large (or small with minithoracotomy) incisions between the ribs to gain access to the thoracic cavity. After the incision, the surgeon separates the ribs with a rib spreader to produce space for insertion of various instruments. The muscles that overlay the chest must be cut during the thoracotomy. Much of the pain during the rehabilitation process is due to the cutting of the muscles. A thoracotomy provides limited access and visualization to the heart unless endoscopes are used. Yet, even the use of endoscopes provides limited access to the posterior regions of the heart and lungs because these organs cannot be lifted or rotated easily.

Thoracostomy techniques use ports through the space created during the thoracotomy. The surgeon uses trocars (e.g. 6-10 mm) to access the thoracic cavity. Access to the anterior surface of the heart is generally sufficient with this technique. However, this technique does not provide ready access or visualization of posterior regions of the heart or other organs. In other words, there is no access to tissue surfaces or organs that are not in a line-of-sight with an axis of the trocar.

In subxyphoid techniques, the surgeon creates an incision below the xyphoid process but above the diaphragm. This technique is common for pericardiocentesis where blood is removed from the pericardial cavity during a pericardial effusion or tamponade. The diaphragm provides a barrier and hindrance to manipulating the heart or accessing the posterior heart surface during subxyphoid techniques. Accordingly, subxyphoid techniques are often limited to procedures that target the anterior or apical ventricular regions.

The conventional surgical techniques discussed do not provide the medical practitioner with optimal visibility of anatomic structures within the thoracic cavity. For example, these procedures do not provide sufficient visibility for anatomic structures located along or adjacent to the posterior surface of the heart or lungs. In order to obtain such visibility, the patient must be placed on cardiopulmonary bypass support. Then the surgeon must create a large incision in the patient's chest through which the patient's heart and lungs can be lifted and/or rotated. Accordingly, surgical practitioners may be hesitant to treat tissues located along or adjacent to the posterior heart or lungs during less invasive procedures, given the inability to visually observe the target area. As such, minimally invasive cardiothoracic surgery has been limited to those anatomic structures located along the anterior surface of the heart.

The novel methods and devices described herein offer improved access to tissue regions within the body when performing minimally invasive procedures through small openings or ports within the body. The devices and methods are not limited to any particular region of the body and can be used in a variety of anatomic regions within the body.

SUMMARY OF THE INVENTION

Methods and devices described herein provide for improved manipulation of organs and/or instruments in the body or within body cavities. The methods and devices may allow for direct visualization if tissue surfaces, organs, other anatomic structures that are not in direct line of sight with the surgical opening.

In one variation, the articulating access device comprises an outer cannula having a rigid proximal portion and a distal portion having a flexible section and a distal tip, a first control member coupled to the outer cannula and extending from the proximal end of the outer cannula to at least the flexible section, the first control member adapted to articulate and maintain the distal portion at an angle relative to the rigid proximal portion by bending the outer cannula at the flexible section, and a flexible inner cannula comprising at least one lumen and having a straight configuration when un-flexed and having a sufficient column strength to permit axial advancement through the outer cannula when the distal portion of the outer cannula is straight or bent, where advancement of the flexible inner cannula through the outer cannula results in a telescopic movement of the flexible inner cannula in a straight line from the distal tip of the outer cannula. In additional variations, the flexible inner cannula can be chosen so that it advances in a curved path rather than a straight line.

Although the access devices illustrated below are shown without handles, variations of the devices can incorporate any number of handle designs where such handel portions are coupled to the outer cannula to aid in placement of the device. Such handle portions can be selected based on the type of procedure being performed.

Variations of the access devices include a second lumen within the flexible inner cannula. The second lumen can be isolated from the main lumen to permit advancement of an instrument or visualization device therethrough without disturbing instruments in the main lumen.

Variations of the access device are steerable through the use of control members. In many variations, the control members are located within the body of the device to prevent interference between the body and the control members. For example, by placing the control members within a wall of the outer cannula (e.g., the control member can include wires, curved tubes, or any other steering mechanism or structure that is conventionally used to steer medical devices). At minimum, the outer cannula will include at least one control member to allow articulation of the distal end in at least one direction. However, any number of control members can be used with the device.

The present invention also includes methods for accessing tissue surfaces within a body of a patient where the tissue surface is obscured by a tissue structure. Such method include advancing an outer cannula through a first opening in the body of the patient, where the outer cannula has a rigid portion and a distal portion, where the distal portion includes a flexible section, manipulating tissue with the rigid portion of the cannula to place the distal portion adjacent to the tissue structure, articulating the distal portion by bending of the flexible section to position a distal opening around the tissue structure, and positioning a working lumen of a flexible inner cannula at the tissue surface by telescopically advancing the flexible inner cannula through the articulated outer cannula, where the flexible inner cannula bends within the flexible section but remains straight upon advancement from the distal opening.

The method can further include coupling a visualization system to the inner cannula. Such visualization systems include scope-type devices. These devices can be inserted into a second lumen in the inner cannula to provide visual access to the tissue surface while not interfering with other devices located within the main lumen.

These additional tools and devices located in the main lumen can be used to perform surgical procedures at the tissue surface.

Variations of the method also include creation of at least a second incision in the patient to provide additional visualization or access of the surgical procedure.

Variations of the access device and procedures described above include combinations of features of the various embodiments or combination of the embodiments themselves wherever possible.

DETAILED DESCRIPTION

Methods and devices described herein provide for improved access of organs or tissue during minimally invasive surgery. Typically, such surgery involves the creation of small incisions or the use of trocars or ports to access regions of the surgical site. However, the devices and methods can also improve access during open surgical procedures by eliminating the need to move organs or dissect significant amounts of tissues when the target site is obscured by tissue structures in the surgical field. For example, in the case of an open chest procedure where a physician accesses the thoracic cavity via a median sternotomy, the use of the devices and methods described herein allow the physician to directly visualize the obscured sides of organs other anatomic structures without the need for excessive manipulation of the organs or tissue structures. As noted above, the methods and devices described herein are not limited to thoracic applications but can be used in any anatomic region of the body.

Figure 1:
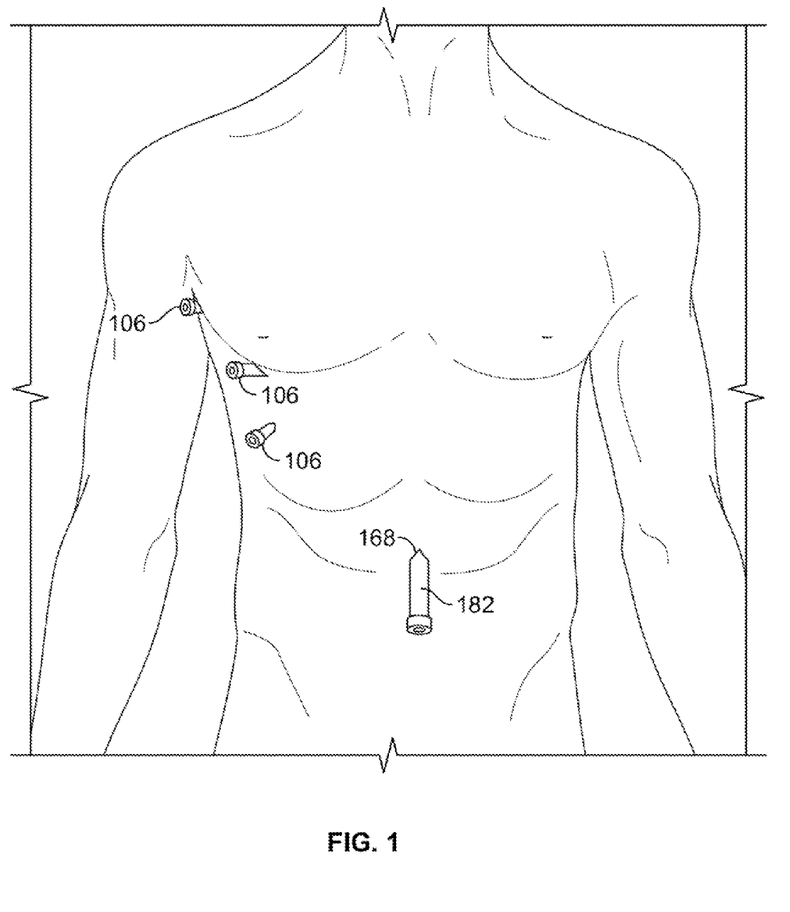
FIG. 1 shows an example of a plurality of openings created in a patients chest or abdomen to provide an entry point for the access devices described herein.

To illustrate this FIG. 1 shows examples of placement of trocars or ports 106 into the chest to provide access to the thoracic cavity. FIG. 1 also show use of an additional access device 182 as described in commonly assigned U.S. application Ser. No. 11/558,417 filed Nov. 9, 2006; Ser. No. 11/408,315 filed Apr. 21, 2006; Ser. No. 11/408,307 filed Apr. 21, 2006; Ser. No. 11/558,417 filed Nov. 9, 2006; Ser. No. 11/558,419 Nov. 9, 2006; and Ser. No. 11/737,493 filed Apr. 19, 2007 ("Diaphragm Entry for Posterior Surgical Access" cases) the entirety of each of which is incorporated by reference. Again, the use of such minimally invasive access point benefits the patient since the openings cause less trauma and improved recuperation times over open surgical procedures. The number and placement of the ports 106 illustrated are intended for illustrative purposes only. Any number of ports may be arranged as needed or as conventionally used.

Figure 2A:
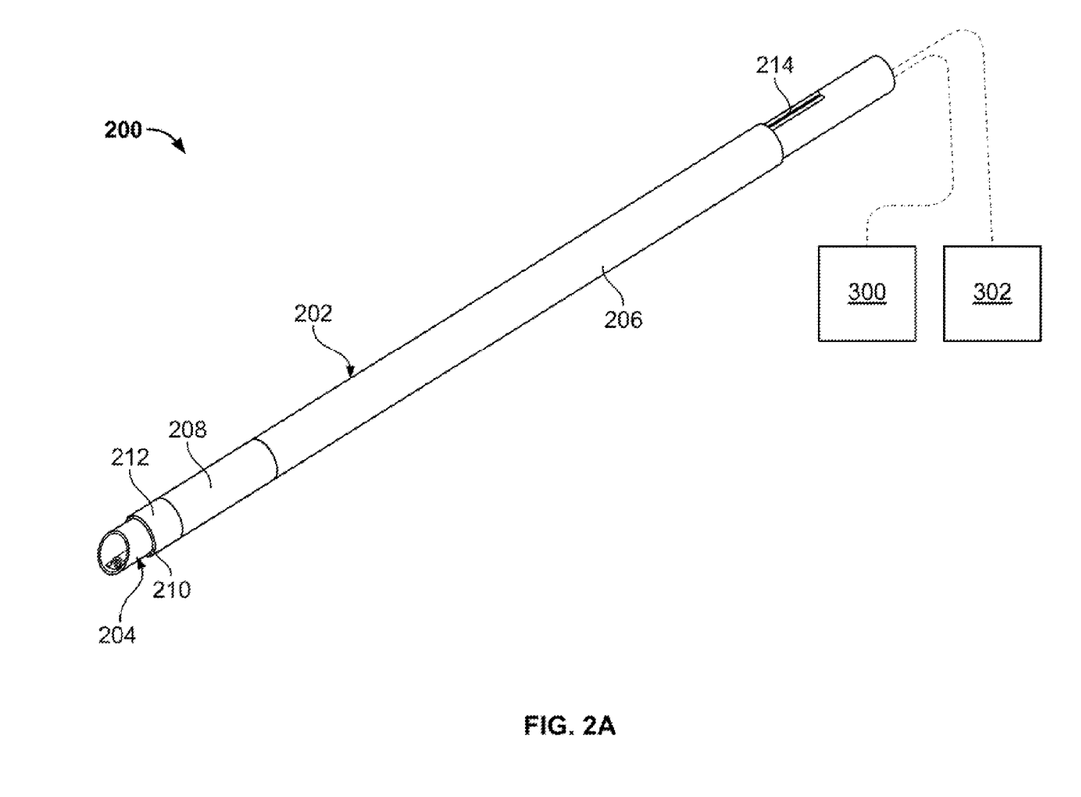
FIG. 2A illustrates a variation of an articulating access device.

FIG. 2A illustrates a variation of art articulating access device 200 according to the principles of the invention. As shown, the access device 200 includes an outer cannula 202 with a flexible inner cannula 204 slidably located therethrough. Variations of the device 200 can include cannulae that are circular in cross section (as shown). In additional variations, the MSS section can be oval, rectangular, or any other shape required by the particular application. Furthermore, the access device 200 can include one or more handles/hubs located on either the inner cannula 204 or outer cannula 202. Such handles are well known by those familiar with the art. For purposes of illustration, the access device 200 is shown without any handles or hubs. However, such structures are not required and the access device can simply consist of the telescoping cannula assembly as shown. The device 200 can also be coupled to a visualization system 300 (e.g., an endoscope, monitor for a camera located at the distal end, or other visualization component). In addition, the device 200 can be coupled to any number of auxiliary components (such as a vacuum source, fluid source, etc.).

The outer cannula 202 comprises a first rigid section 206. The rigid section 206 can optionally comprise a hard outer shell. However, in any case, the rigid section 206 is sufficiently rigid such that a physician can advance and manipulate the cannula remotely (from the proximal end) through a body cavity and through tissue or other organs. In such cases, the physician might need to use the rigid section 206 to move or dissect organs to properly position the opening 210 of the cannula 202 The distal portion of the cannula 202 comprises a flexible section 208 located proximate to the opening 210. In most variations, the rigid section 206 of the outer cannula 202 is straight. However, the rigid section 206 can include curved or angled profiles as required by the particular surgical application or the target anatomy.

As discussed below, configuring an articulating device to have a flexible section 208 distal to the rigid section 206 in a distal portion of the device 200 permits repositioning of the opening 210 around tissue and other structures within the body. The rigid nature of the outer cannula permits the physician to leverage the device into position (typically by manipulating the device from outside of the body through a port or small incision.) The relative movement between the flexible inner cannula 204 and the outer cannula 202 allows the physician to telescopically advance the opening of the inner cannula 204 to the desired target site and reach organs and surfaces that are not in alignment with the surgical opening.

In the variation shown, distal portion of the outer cannula 202 includes a rigid tip 212 adjacent to the opening 210 and distal to the flexible section 208. In alternate variations, the flexible section 208 can extend through the entire distal section of the cannula 202.

The outer cannula 202 also includes one or more control members 214 that permit flexing or articulation of the cannula 202 at the flexible section 208. The control member 214 can include any steering mechanism or structure that is conventionally used to steer medical devices. However, in this variation, the control member 214 comprises a pair of wires coupled to the distal tip 212 of the outer cannula 202. Although not shown, the control member 214 can include any number of features to assist in positioning of the opening 210. For example, the control members can be dial, lever, or trigger actuated with an optional ratcheting mechanism to control the articulation of the cannula 202. Clearly, the articulating access device can be combined with any number of similar features known by those skilled in the art. For example, such structures are described in U.S. Pat. No. 3,470,876 to Barchilon; U.S. Pat. No. 4,690,411 to Buchbinder; U.S. Pat. No. 4,898,577 to Badger et al.; U.S. Pat. No. 4,960,134 to Webster; U.S. Pat. No. 5,325,845 to Adair; and U.S. Pat. No. 6,953,454 to Peterson et al. Each of which is incorporated by reference.

Figure 2B:
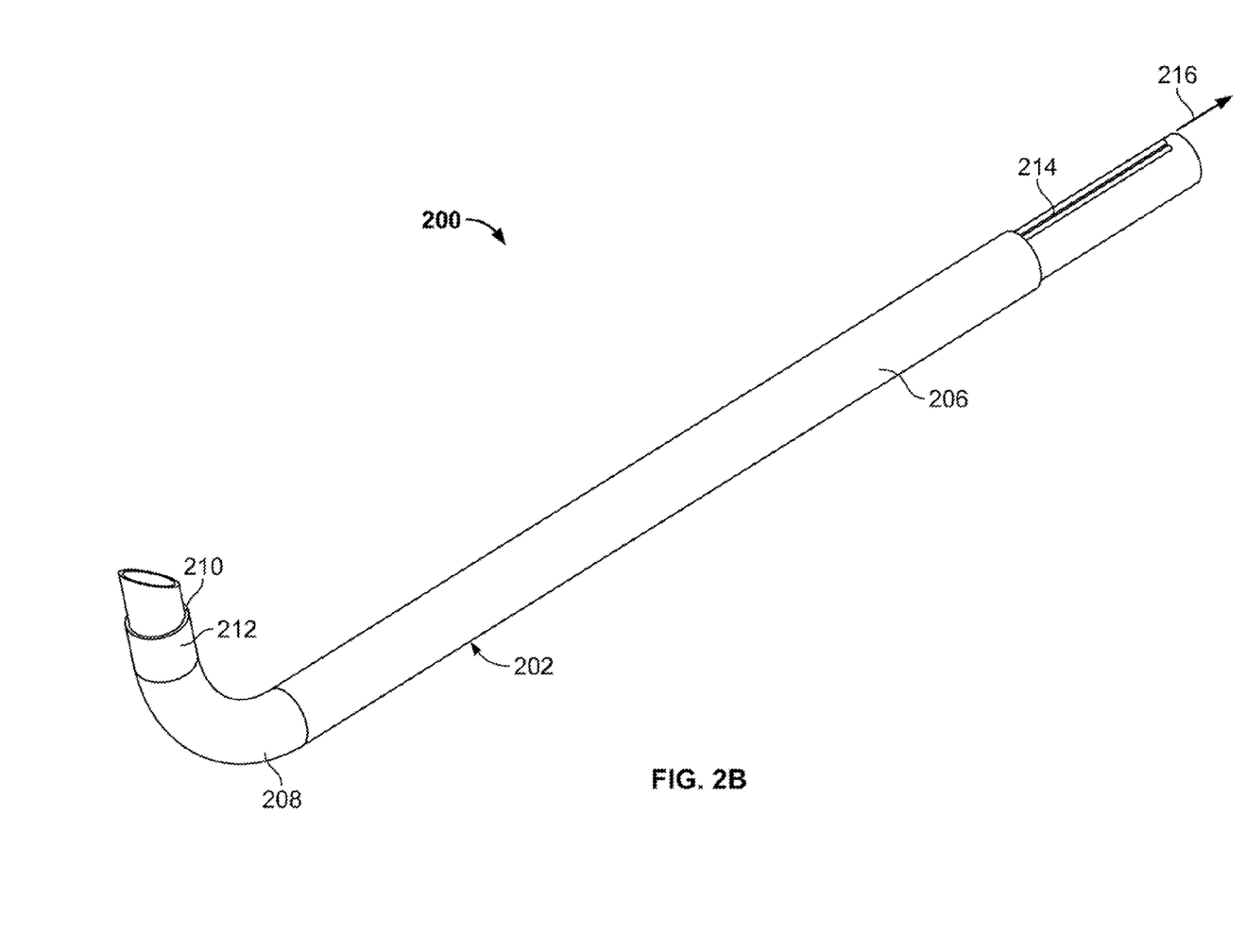
FIG. 2B shows a perspective view of the device of FIG. 2A where actuation of the control member causes the cannula to articulate at a flexible section of the distal portion.

FIG. 2B shows a perspective view of the device 200 of FIG. 2A where actuation of the control member 214 (in this variation, in the direction of arrow 216) causes the cannula 202 to articulate at a distal portion. As shown, the cannula 202 bends at the flexible section 208 so that the physician can reposition the opening 210 of the access device 202 out of alignment with an axis of the proximal end of the cannula 202 (and thus away from an axis of any entry incision or trocar.) In order to optimally navigate around tissue structures or other obstructions, the control member 214 is encased within the cannula 202. Alternatively, the control member 214 can be exterior to the cannula or within a passageway of the cannula as long as operation of the control member 214 does not interfere against tissue or structures when actuating the device 200.

Figure 2C:
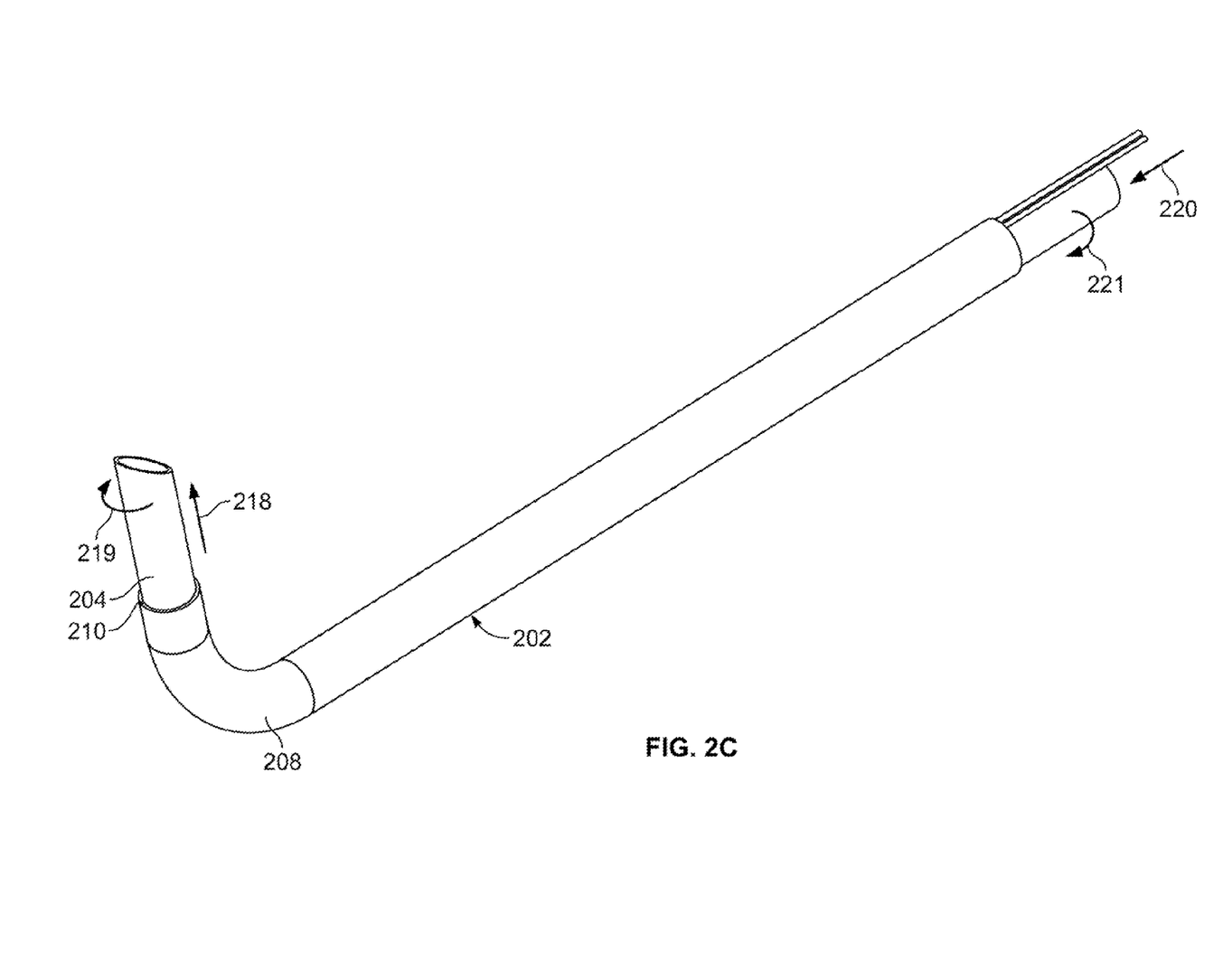
FIG. 2C shows the device of FIG. 2B after the flexible inner cannula advances out of the outer cannula in a telescopic type motion.

FIG. 2C shows the device of FIG. 2B after the flexible inner cannula 204 advances out of the opening 210 in a telescopic type motion 218 when a physician advances the cannula 204 at a proximal end as shown by arrow 220. The inner cannula 204 can be completely flexible such that it can advance through the flexible section 208 of the outer cannula 202 regardless of the direction of articulation of the outer cannula 202. In one variation, the flexible inner cannula 204 comprises a linear shape when up-flexed or when in natural state. Accordingly, as the inner cannula 204 advances from the opening 210, it advances in a straight line configuration. The device 200 can also be configured so that rotation of the proximal end of the flexible cannula 204 (as shown by arrow 221) causes rotation of the distal portion of the flexible cannula 204 (as shown by arrow 219). In such variations, while the flexible inner cannula 204 is fabricated to advance through the articulated outer cannula 202, the flexible inner cannula 204 will be fabricated so that rotation of the proximal end translates into a near one-to-one rotation of the distal end.

Figure 2D:
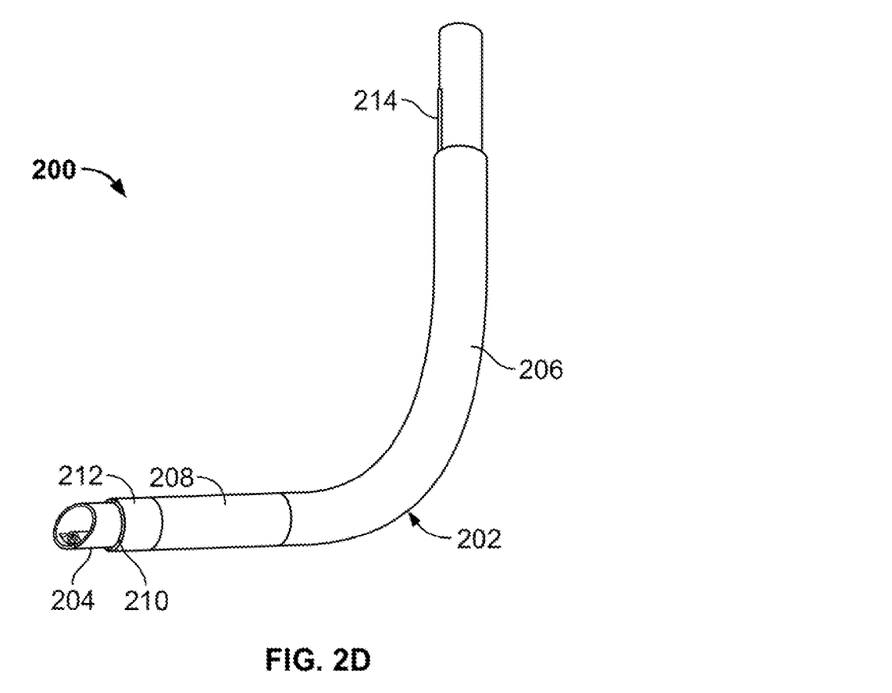
FIGS. 2D and 2E illustrate variations of an articulating access device having curved or angled rigid proximal sections.
Figure 2E:
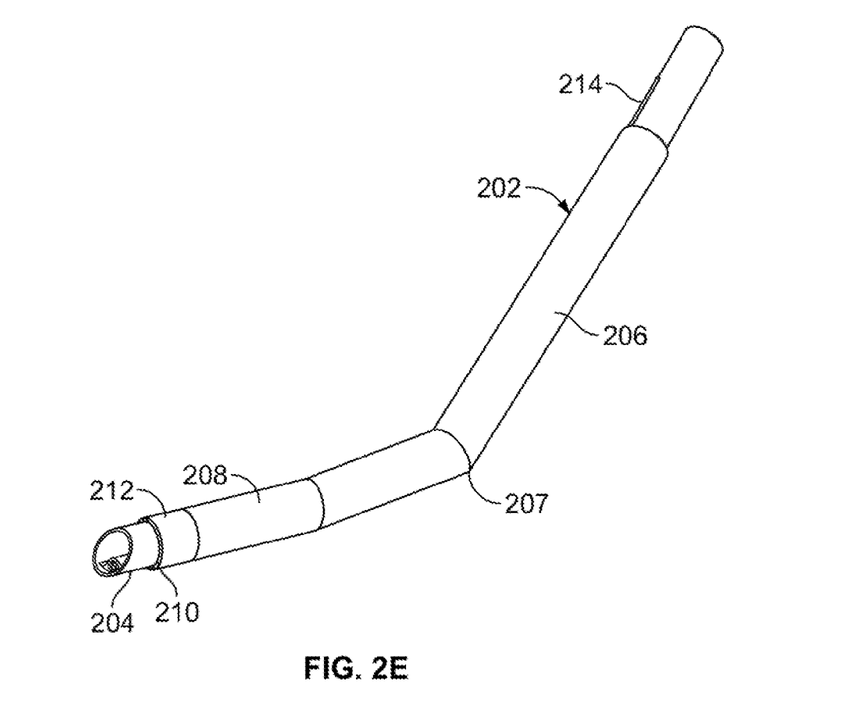

FIGS. 2D and 2E illustrate variations of the articulating access device 200 where the rigid proximal section 206 of the outer cannula 202 is curved (FIG. 2D) or has a bend 207 (FIG. 2E). Naturally, any number of combinations of shapes for the rigid proximal section 206 is possible and within the scope of the device described herein. In any case, the flexible inner cannula 204 accommodates the curve or bends in the rigid section 206 and further bends to accommodate the articulation of the flexible section 208. In most variations, as the physician advances the flexible inner cannula 204 from the distal opening 210 of the outer cannula 204, the flexible inner cannula 204 assumes its straight configuration for telescopic advancement from the opening 210.

Figure 3A:
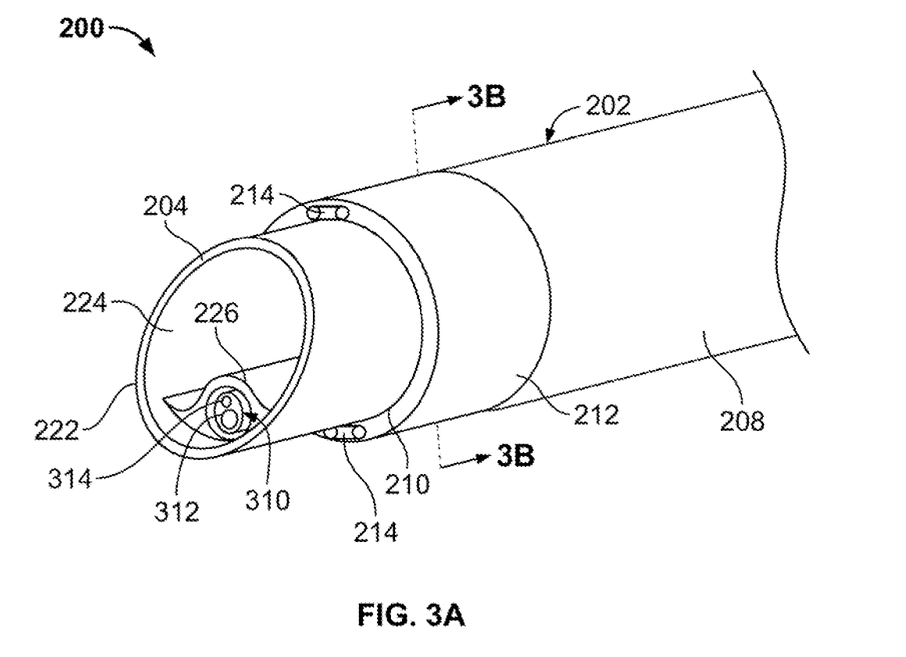
FIG. 3A shows a perspective view of a distal portion of an access device.

FIG. 3A shows a perspective view of a distal portion of an access device 200. As illustrated, a pair of control members 214 is coupled to the distal tip 212 of the cannula 202. In this case, the control member 214 comprises wires on opposite sides of the outer cannula 202 to allow movement in at least two directions. Clearly, any number of control members is within the scope of this disclosure.

The flexible inner cannula 204 comprises a tapered opening 222 at the end of a passageway or working lumen 224 that extends through the inner cannula 204. A tapered opening allows for an increased open area. This increase in area is beneficial when advancing multiple devices through the cannula 204. Moreover, the tapered tip helps to advance the device through the tissue by allowing the physician to gently dilate the tissue as the tip is inserted. The tapered tip also helps with visualization, as it allows structures that are not in line with the opening, to be viewed.

The flexible inner cannula 204 can also include a second lumen 226 separate from the main lumen 224. The second lumen 226 can be fluidly isolated or may simply be a support frame that permits one or more tools to be placed within the lumen 226 without interfering with other instruments that are within the main lumen 224. In the illustrated variation, the second lumen 226 includes a flexible visualization type device 310 (e.g., one having a visualization element 312 and/or an illumination source 314). The visualization device 310 can comprise an endoscope type device or may be a video chip integrated within the channel. In any case, the visualization type device 310 allows the physician to remotely view the area adjacent to the opening of the second lumen 226. The visualization source 310 can be advanced with the device 200 or may be advanced once the device 200 is placed within the body. Furthermore, as shown, the second lumen 226 and visualization device 310 are shown to be recessed or offset from the end 222 of the inner cannula 204. This offset allows for the visualization device 310 to observe other instruments that are advanced through the main lumen for performing various surgical or diagnostic procedures. In addition, recessing; the visualization device recessed reduces the chance that tissue will from wiping against the visualization device and obscure the view.)

Figure 3B:
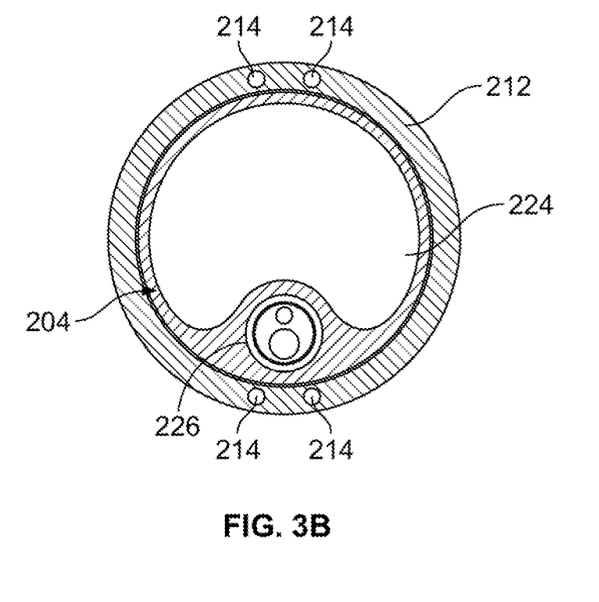
FIG. 3B shows a cross sectional view taken along lines 3B-3B of FIG. 3A.

FIG. 3B shows a cross sectional view taken along lines 3B-3B of FIG. 3A. In this variation, the main lumen 224 and second lumen 226 extend parallel to each other. However, in certain variations, the main lumen and second lumen can be coaxial in alternate variations, the device can include various additional lumens (e.g., for suction, fluid delivery, delivery of therapeutics, etc.).

Figure 4A:
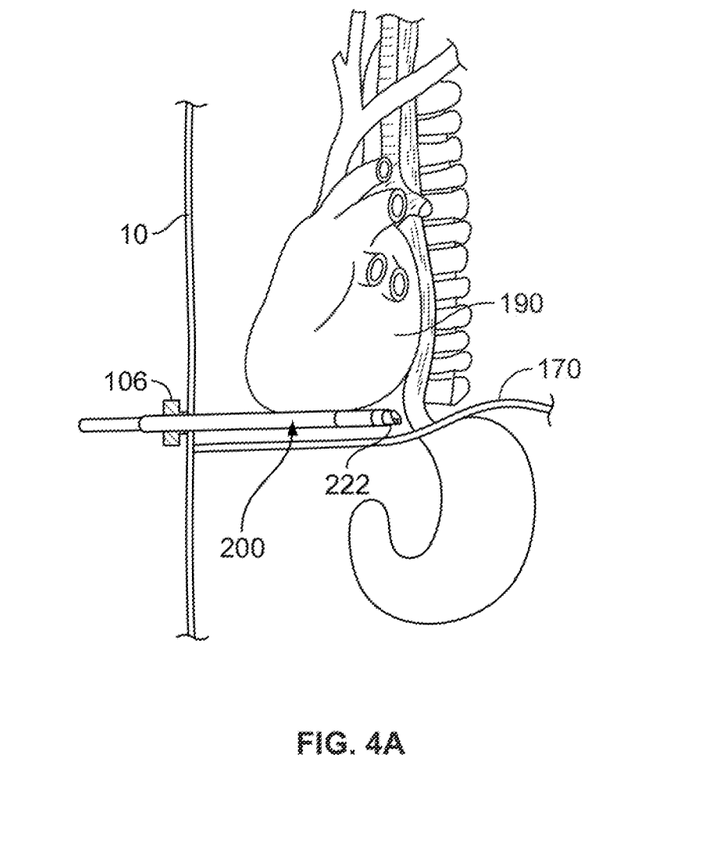
FIGS. 4A to 4C illustrates one example of an articulating access device used to access regions of the body not in alignment with an axis of the entry point, port, or incision.
Figure 4B:
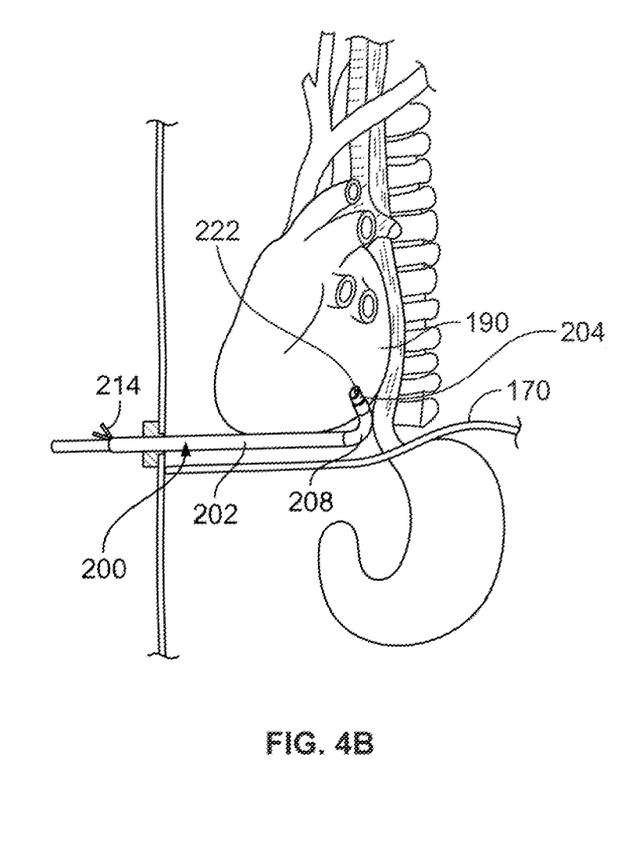
Figure 4C:
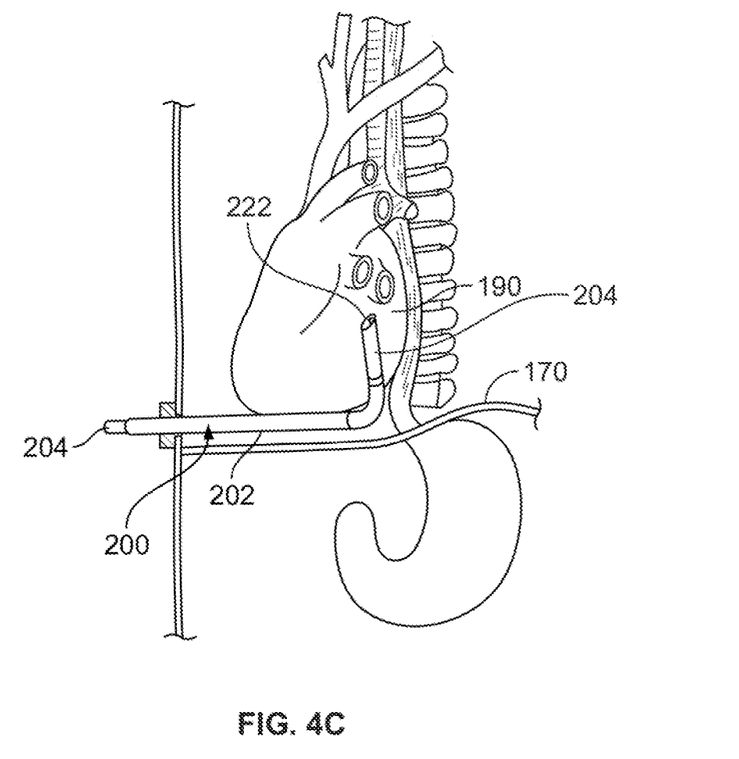

FIGS. 4A to 4C illustrates an example of the articulating access device 200 when used to access regions of the body that are not aligned with an axis of the entry point or port 106. These figures are for illustrative purposes only. More importantly, although the access device 200 is shown as accessing the thoracic cavity through the chest wall 10, the device 200 can be used in any anatomic region of the body. In one such variation, the device can be used with additional techniques to provide multiple points of access to a surgical site. For example, as taught in the "Diaphragm Entry for Posterior Surgical Access" cases cited above, alternate devices are used to access posterior surfaces of organs within the thoracic cavity. Use of the articulating access device 200 in addition provides the physician with an ability to locate additional tissue regions that would otherwise be obscured.

As shown in FIG. 4A, a physician advances the access device 200 through the chest wall 10 (either through a trocar/port 106 or through an incision). The physician is able to manipulate organs due to the rigid portion of the device 200 when placing the distal portion of the device as desired. For example, in the illustrated variation, the rigid cannula can be used to manipulate cardiac tissue or the diaphragm 170 when placing the device. As noted above, the inner cannula typically contains a visualization device (not shown). In this variation, the visualization permits the physician to locate the opening 222 of the inner cannula at a posterior ventricular surface 190.

FIG. 4B illustrates the state of the device 200 when the physician actuates the control members 214 to bend the device at a flexible section 208 of the distal portion of the outer cannula 202. As shown, this permits the opening 222 of the inner cannula 204 to curve around the heart to access a posterior ventricular surface 190.

FIG. 4C shows advancement of the opening 222 of the inner cannula 204 when the physician advances the inner cannula from outside of the body. As noted above, because the inner cannula 204 is flexible, but returns to its initial straight shape upon leaving, the outer cannula 202, the opening 222 of the inner cannula 204 advances in a straight line towards the desired region. Again, this advancement is typically performed under indirect visualization. As shown, the opening 222 of the inner cannula 204 is now located at a region that would have otherwise been inaccessible due to the presence of organs and tissue structures within the body.

As discussed above, the access device 200 can include a locking mechanism so that the physician can advance additional instruments or devices through the main lumen of the inner cannula 204 to perform various medical diagnostic or procedures.

The invention contemplates use of any surgical device that may be advanced through the access device to perform any procedure that benefits from having improved access as described herein. The integrated vacuum coagulation probe embodiments in commonly assigned co-pending U.S. application Ser. No. 10/425,251 filed Apr. 29, 2003; Ser. No. 11/208,465 filed Aug. 18, 2005; Ser. No. 11/408,302 filed Apr. 21, 2006; Ser. No. 11/558,420 filed Nov. 9, 2006; and Ser. No. 11/737,523 filed Apr. 19, 20071; U.S. Pat. No. 6,893,442; and PCT Application No. PCT/US2006/015009 filed Apr. 21, 2006 (Each of which is incorporated by reference here) are also examples of devices that can be used with the access devices described herein. Such probes provide examples of devices that allow intimate contact specifically between a soft tissue surface and the energy portion of the device. In those example, the electrode(s) used to transmit energy (radiofrequency or ultrasonic) is capable of heating the soft tissue until achieving irreversible injury making the soft tissue non-viable and unable to propagate electrical impulses, mutate, or reproduce. These integrated vacuum coagulation probe embodiments may be used with the articulating access device to coagulate soft tissue capable of treating atrial fibrillation, ventricular tachycardia or other arrhythmia substrate, or eliminating cancers (such as lung cancer), or other soft thoracic tissue by destroying target cells.

In addition, these integrated vacuum coagulation devices may be used to heat soft tissue along the posterior heart surface resulting in heat-induced contraction of collagen in such tissue thereby resulting shrinking of said soft tissue. For example, heating the mitral valve annulus along the posterior atrio-ventricular groove may induce shrinking of the annulus thereby correcting mitral valve regurgitation. However, it is understood that the invention is not limited to the above described vacuum coagulation probes. Instead, any number of coagulation, ablation, or surgical devices may be used as required.

What is claimed is:

1. An articulating telescopic medical access device comprising:
    an outer cannula having a rigid proximal portion and a distal portion having a flexible section and a distal tip;
    a first control member coupled to the outer cannula and extending from the proximal end of the outer cannula to at least the flexible section, the first control member adapted to articulate and maintain the distal portion at an angle relative to the rigid proximal portion by bending the outer cannula at the flexible section; and
    a flexible inner cannula comprising at least one lumen and having a straight configuration when un-flexed and having a sufficient column strength to permit axial advancement through the outer cannula when the distal portion of the outer cannula is straight and when the distal portion of the outer cannula is bent, where advancement of the flexible inner cannula through the outer cannula results in a telescopic movement of the flexible inner cannula in a straight line from the distal tip of the outer cannula.

2. The access device of claim 1, further comprising a handle portion coupled to the proximal portion of the outer cannula.

3. The access device of claim 1, where the flexible inner cannula further comprises a second lumen isolated from the at least one lumen of the flexible inner cannula.

4. The access device of claim 1, further comprising a video source located within the flexible inner cannula.

5. The access device of claim 1, where a distal end of the flexible inner cannula comprises a beveled tip.

6. The access device of claim 1, where the distal tip is rigid and where the flexible section of the distal portion is adjacent to the distal tip.

7. The access device of claim 1, where the distal tip comprises a beveled tip.

8. The access device of claim 1, where the rigid proximal portion is straight.

9. The access device of claim 1, where the rigid proximal portion is curved.

10. The access device of claim 1, where the rigid proximal portion is angled.

11. The access device of claim 1, where the control member extends through a wall of the outer cannula.

12. The access device of claim 11, where the control member comprises at least one elongate member affixed to the distal tip, where proximal movement of the elongate member causes bending of the distal portion of the outer cannula.

13. The access device of claim 11, further comprising a second control member and where the first control member and the second control member are affixed to the distal tip, where proximal movement of the elongate member causes bending of the distal portion of the outer cannula.

* * * * *